(12) United States Patent
Nguyen et al.

(10) Patent No.: US 11,875,877 B2
(45) Date of Patent: Jan. 16, 2024

(54) IMMUNOTHERAPY MARKERS AND USES THEREFOR

(71) Applicant: NantOmics, LLC, Culver City, CA (US)

(72) Inventors: Andrew Nguyen, San Jose, CA (US); John Zachary Sanborn, Santa Cruz, CA (US); Shahrooz Rabizadeh, Los Angeles, CA (US)

(73) Assignee: NantOmics, LLC, Culver City, CA (US)

( * ) Notice: Subject to any disclaimer, the term of this patent is extended or adjusted under 35 U.S.C. 154(b) by 236 days.

(21) Appl. No.: 16/327,802

(22) PCT Filed: Aug. 25, 2017

(86) PCT No.: PCT/US2017/048629
§ 371 (c)(1),
(2) Date: Feb. 22, 2019

(87) PCT Pub. No.: WO2018/039567
PCT Pub. Date: Mar. 1, 2018

(65) Prior Publication Data
US 2019/0237196 A1    Aug. 1, 2019

Related U.S. Application Data

(60) Provisional application No. 62/379,700, filed on Aug. 25, 2016.

(51) Int. Cl.
| | |
|---|---|
| *G16B 25/10* | (2019.01) |
| *G16B 30/10* | (2019.01) |
| *G16B 20/00* | (2019.01) |
| *G16H 50/30* | (2018.01) |
| *G16H 50/20* | (2018.01) |
| *G16B 20/20* | (2019.01) |
| *G16B 40/00* | (2019.01) |
| *C12Q 1/6827* | (2018.01) |
| *C12Q 1/6869* | (2018.01) |

(52) U.S. Cl.
CPC ............ *G16B 25/10* (2019.02); *C12Q 1/6827* (2013.01); *C12Q 1/6869* (2013.01); *G16B 20/00* (2019.02); *G16B 20/20* (2019.02); *G16B 30/10* (2019.02); *G16B 40/00* (2019.02); *G16H 50/20* (2018.01); *G16H 50/30* (2018.01); *G01N 2570/00* (2013.01); *Y02A 90/10* (2018.01)

(58) Field of Classification Search
None
See application file for complete search history.

(56) References Cited

U.S. PATENT DOCUMENTS

| | | |
|---|---|---|
| 7,473,532 B2 | 1/2009 | Darfler et al. |
| 9,091,651 B2 | 7/2015 | Kearney et al. |
| 2012/0059670 A1 | 3/2012 | Sanborn et al. |
| 2012/0066001 A1 | 3/2012 | Sanborn et al. |
| 2015/0284803 A1 | 10/2015 | Lindley |
| 2015/0354009 A1 | 12/2015 | Sadanandam et al. |
| 2017/0032082 A1 | 2/2017 | Nguyen et al. |
| 2017/0065693 A1 | 3/2017 | Balint et al. |
| 2017/0165341 A1 | 6/2017 | Jones et al. |

FOREIGN PATENT DOCUMENTS

| | | |
|---|---|---|
| AU | 2006338523 A8 | 7/2008 |
| AU | 2017315468 B2 | 2/2020 |
| CA | 3 034 771 A1 | 3/2018 |
| CN | 109937452 A | 6/2019 |
| JP | 2019-534685 A | 12/2019 |
| KR | 10-2019-0038935 A | 4/2019 |
| KR | 10-2020-0003294 A | 1/2020 |
| WO | 2011/139345 A3 | 3/2012 |
| WO | 2013/062505 A1 | 5/2013 |
| WO | 2015069770 A1 | 5/2015 |
| WO | 2016/077709 A1 | 5/2016 |
| WO | 2016/081947 A2 | 5/2016 |
| WO | 2016100975 A1 | 6/2016 |
| WO | 2017/004165 A1 | 1/2017 |
| WO | 2017/004181 A1 | 1/2017 |
| WO | 2017/031551 A1 | 3/2017 |
| WO | 2017/087819 A1 | 5/2017 |
| WO | 2018/027076 A1 | 2/2018 |
| WO | 2018/039567 A1 | 3/2018 |

OTHER PUBLICATIONS

Walker et al APOBEC family mutational signatures are associated with poor prognosis translocations in multiple myeloma, Nature Communications vol. 6, Article No. 6997 (2015).*
Cescon et al APOBEC3B expression in breast cancer reflects cellular proliferation, while a deletion polymorphism is associated with immune activation PNAS | Mar. 3, 2015 | vol. 112 | No. 9 | 2841-2846.*
Helleday et al. Mechanisms underlying mutational signatures in human cancers Nature Reviews | GENETICS vol. 15 | Sep. 2014.*
Seplyarskiy et al. APOBEC-induced mutations in human cancers are strongly enriched on the lagging DNA strand during replication Genome Research 26:174-182 Published by Cold Spring Harbor Laboratory Press; ISSN 1088-9051/16.*
Snyder et al. Genetic Basis for Clinical Response to CTLA-4 Blockade in Melanoma N Engl J Med 371;23 (2014).*

(Continued)

*Primary Examiner* — Joseph Woitach
(74) *Attorney, Agent, or Firm* — Martin Fessenmaier; Umberg Zipser LLP

(57) ABSTRACT

Systems and methods for prediction of the treatment outcome for immune therapy are presented in which omics data of a patient tumor sample are used. Most typically, the omics data are processed to identify mutational signatures (especially APOBEC/POLE signatures), immune checkpoint expression, and MSI status as leading indicators to predict the treatment outcome for immune therapy. Such prediction advantageously integrates various parameters that would otherwise, when individually considered, skew prediction outcome.

7 Claims, 1 Drawing Sheet

(56) References Cited

OTHER PUBLICATIONS

Le et al. PD-1 Blockade in Tumors with Mismatch-Repair Deficiency N Engl J Med 372;26 (2015).*
Schrock et al. Characterization of 298 Patients with Lung Cancer Harboring MET Exon 14 Skipping Alterations Journal of Thoracic Oncology vol. 11 No. 9: 1493-1502.*
Gubin et al Science vol. 350 iss 6257 (2015).*
Russell et al., "Oncolytic virotherapy", Nat Biotechnol., 2014, vol. 30, No. 7, 31 pages (Cited from Specification).
Lechner et al., "Immunogenicity of murine solid tumor models as a defining feature of in vivo behavior and response to Immunotherapy", Journal of Immunotherapy, 2013, vol. 36, No. 9, pp. 477-489 (Cited from Specification).
Palles et al., "Germline mutations affecting the proofreading domains of POLE and POLD1 predispose to colorectal adenomas and carcinomas", Nat Genet., Feb. 2013, vol. 45, No. 2, 21 pages (Cited from Specification).
Ciriano et al., "A molecular portrait of microsatellite instability across multiple cancers", Nature Communications, 2017, 12 pages.
Examination Report received for Australian Patent Application Serial No. 2017315468 dated Apr. 2, 2019, 3 pages.
Notice of Acceptance received for Australian Patent Application Serial No. 2017315468 dated Jan. 29, 2020, 3 pages.
Office Action received for Canadian Patent Application Serial No. 3034771 dated Apr. 3, 2020, 5 pages.
Extended European Search Report received in European Patent Application Serial No. 17844492.3 dated Apr. 2, 2020, 14 pages.
Boichard et al., "High Expression of PD-1 Ligands is Associated with Kataegis Mutational Signature and APOBEC3 Alterations", OncoImmunology, 2017, 39 pages.
Howitt et al., "Association of Polymerase e-Mutated and MicrosatelliteInstable Endometrial Cancers With Neoantigen Load, Number of Tumor-Infiltrating Lymphocytes, and Expression of PD-1 and PD-L1", Jama Oncology, Jul. 9, 2015, pp. E1-E5.
Mehnert et al., "Immune activation and response to pembrolizumab in POLE-mutant endometrial cancer", The Journal of Clinical Investigation, Jun. 2016, vol. 126, No. 6, pp. 2334-2340.
Notice of Final Rejection received in Korean Patent Application Serial No. 1020197008366 dated Oct. 16, 2019, 7 pages (Including English Translation).
International Search Report and Written Opinion received for PCT Application Serial No. PCT/US2017/048629 dated Jan. 30, 2018, 14 pages.
International Preliminary Report on Patentability Chapter II received for PCT Application Serial No. PCT/US2017/048629 dated Dec. 18, 2018, 14 pages.
Roberts et al., "Pan-Cancer Analysis of APOBEC Mutagenesis", National Institute of Environmental Health Sciences, 2013, 14 pages.
Hsu et al., "TCR Sequencing Can Identify and Track Glioma-Infiltrating T Cells after DC Vaccination", Cancer Immunology Research, May 2016, vol. 4, No. 5, pp. 412-418 (Cited from Specification).
English Translation of Office Action received in Korean Application No. 10-2019-7008366 dated Jul. 16, 2019.
R. M. Chabanon et al., "Mutational Landscape and Sensitivity to immune Checkpoint Blockers", Author Manuscript, American Association for Cancer, Jul. 7, 2016.
R. Mandal et al., "Personalized Oncology Meets Immunology: The Path toward Precision Immunotherapy", Cancer Discovery Jul. 2016, pp. 703-713, Apr. 22, 2016.
Communication under Rule 71(3) EPC received for European Patent Application Serial No. 17844492.3 dated Feb. 22, 2021, 8 pages.
Notice of Reasons for Refusal received for Japanese Patent Application Serial No. 2019510972 dated Feb. 2, 2021, 7 pages (Including English Translation).
Office Action received for Canadian Patent Application Serial No. 3034771 dated Nov. 3, 2020, 4 pages.
Notice of Reasons for Refusal received for Japanese Patent Application Serial No. 2019510972 dated Sep. 8, 2020, 7 pages (Including English Translation).
Gargiulo et al., "Tumor genotype and immune microenvironment in POLE-ultramutated and MSI-hypermutated Endometrial Cancers: New candidates for checkpoint blockade immunotherapy?", Cancer Treat Rev., 2016, vol. 48, pp. 61-68.
Xuan et al., "APOBEC3 deletion polymorphism is associated with breast cancer risk among women of European ancestry", Carcinogenesis, 2013, vol. 34, No. 10, pp. 2240-2243.
Rebhandl et al., "APOBEC3 signature mutations in chronic lymphocytic leukemia", Leukemia, 2014, vol. 28, No. 9, pp. 1929-1932.
Seplyarskiy, V. et al., APOBEC-induced mutations in human cancers are strongly enriched on the lagging DNA strand during replication, Genome Research, Aug. 16, 2016, pp. 1-9.
Roberts, S. et al., An APOBEC Cytidine Deaminase Mutagenesis Pattern is Widespread in Human Cancers, Nat Genet., Sep. 2013, 45(9) pp. 970-976, NIH Public Access.
Alexandrov, L., et al., Signatures of mutational processes in human cancer, Nature, Aug. 22, 2013, 500 pp. 1-24.
Walker, B. et al., APOBEC family mutational signatures are associated with poor prognosis translocations in multiple myeloma, Nature Communications, Apr. 23, 2015, pp. 1-11.
Gordenin, D. et al., Pan-Cancer Analysis of APOBEC Mutagenesis, NIEHS (14 pages).
Haradhvala, N., Mutational Strand Asymmetries in Cancer Genomes Reveal Mechanisms of DNA Damage and Repair, Cell, 164, Jan. 28, 2016, pp. 538-549.
Xiao, Y. et al., The Microsatellite Instable Subset of Colorectal Cancer Is a Particularly Good Candidate for Checkpoint Blockade Immunotherapy, Cancer Discovery, pp. 16-18.
Mullane et al., "Correlation of Apobec Mrna Expression with overall Survival and pd-l1 Expression in Urothelial Carcinoma", Scientific Reports, 2016, vol. 6, No. 27702, pp. 1-7.

* cited by examiner

Immunotherapy markers

This analysis examines the contribution of MSI status, POLE/APOBEC mutation rate and mutational signatures and immune checkpoint expression for sensitivity towards an immunotherapy approach.

This sample contains 3 of 4 indicators that suggests sensitivity to immunotherapy.

Immunotherapy sensitivity markers.

| Marker | Status | Immunotherapy Permissive |
|---|---|---|
| MSI Status | Microsatellite Stable. | No |
| APOBEC/POLE Mutation Signature | 1 of 3 Significant POLE/APOBEC Signatures found. | Yes |
| Mutation Rate | 3.71 per Megabase coding DNA | Yes |
| Immune Checkpoint Expression | 5 of 9 immune checkpoint related genes over-expressed. | Yes |

Immunotherapy related gene expression.

| Checkpoint Gene | Common Name | Function | Status | TPM |
|---|---|---|---|---|
| IDO1 | IDO | Immune Escape Signal | Normal | 85.55 |
| HAVCR2 | TIM3 | Immune checkpoint | Normal | 27.57 |
| CD40 | CD40 | Immune Escape Signal | Normal | 24.92 |
| LAG3 | LAG3 | Immune Checkpoint | Over-expressed | 22.98 |
| PDCD1LG2 | PDL2 | Immune Checkpoint Ligand | Over-expressed | 20.98 |
| CD274 | PDL1 | Immune Checkpoint Ligand | Over-expressed | 16.42 |
| CTLA4 | CTLA4 | Immune Checkpoint | Over-expressed | 8.39 |
| PDCD1 | PD1 | Immune Checkpoints | Over-expressed | 5.51 |
| IL2 | IL2 | Immune Stimulatory Signal | Normal | 0.21 |

IMMUNOTHERAPY MARKERS AND USES THEREFOR

This application claims priority our US provisional application with the Ser. No. 62/379,700, filed Aug. 25, 2016.

FIELD OF THE INVENTION

The field of the invention is computational analysis of omics data to allow for patient stratification with respect to immune therapy, especially where such therapy uses checkpoint inhibition in addition to a vaccine composition and/or cell-based composition.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Immune therapy using genetically modified viruses has become a conceptually effective and attractive route for treatment of various cancers. However, numerous challenges remain to be resolved. For example, the choice of suitable antigens to be expressed is non-trivial (see e.g., *Nat Biotechnol.* 2012 Jul. 10; 30(7):658-70). Moreover, even frequently expressed epitopes will not guarantee a strong and tumor-protective immune reaction in all patients. In addition, even where several neoepitopes are known and used as an immunotherapeutic composition, various inhibitory factors may nevertheless prevent a therapeutically effective response. For example, a sufficient immune response may be blunted or even prevented by Tregs (i.e., regulatory T cells) and/or MDSCs (myeloid derived suppressor cells). In addition, lack of stimulatory factors and tumor based interference with immune checkpoints, and especially PD-1 and CTLA-4, may still further prevent a therapeutic response to immune therapy.

While various therapeutic compositions are known in the art to block or silence immune checkpoints (e.g., Pembrolizumab or Nivolumab for PD-1 system, or Ipilimumab for the CTLA-4 system), administration is not consistently effective to promote a durable and therapeutically useful response. Notably, such compounds have demonstrated extensive activity as single agents and in combinations, and clinical responses have been seen in some cases of melanoma, renal cell carcinoma, non-small cell lung cancer, and various other tumor types. Unfortunately however, not all types of cancers respond equally well to treatment with checkpoint inhibitors, and positive response predictability has been elusive.

More recently, a predictive model was proposed that used tumor MHC-I expression as a positively correlated marker with overall tumor immunogenicity (see *J Immunother* 2013, Vol. 36, No 9, p 477-489). The authors also noted a pattern in which certain immune activating genes were up-regulated in strongly immunogenic tumors of some of the models, but advised that additional biomarkers should be found to help predict immunotherapy response. In another approach (*Cancer Immunol Res;* 4(5) May 2016, OF1-7), post-treatment in depth sequence and distribution analysis of tumor reactive T cell receptors indicated was used as a proxy indicator for reactive T-cell tumor infiltration. Unfortunately, such analysis fails to provide predictive insight with respect to likely treatment success for immune therapy, and especially immune therapy that uses a vaccine component and/or a cell-based component.

In another example, as described in US20170032082, the number of immunologically visible neoepitopes was used as a predictive marker for likely positive outcome of a treatment with checkpoint inhibitors where the number exceeded a predetermined threshold. Moreover, such methods additionally included in at least some aspects a determination of microsatellite instability. While such analysis advantageously considered the HLA type of the patient, and with that the visibility of neoepitopes, the predicted treatment outcome was generally limited to the use of checkpoint inhibitors.

Thus, even though various systems and methods of immune therapy for many cancers are known in the art, all or almost all of them suffer from several drawbacks. Therefore, there is still a need to provide improved systems and methods to more accurately predict the likely outcome of immune therapy, especially where such therapy uses checkpoint inhibition in addition to a vaccine composition and/or cell-based composition.

SUMMARY OF THE INVENTION

The inventive subject matter is directed to various systems and methods of analysis of omics data to predict likely treatment success to immune therapy. Computational analysis is preferably performed on omics data obtained from a tumor to so identify MSI (microsatellite instability) status, mutational signatures (and particularly APOBEC and/or POLE signatures), and/or immune checkpoint expression. Advantageously, such analysis will integrate various features that, when considered individually, will not allow for a reliable outcome prediction for immunotherapy that uses in addition to checkpoint inhibition a vaccine component and/or a cell-based component.

In one aspect of the inventive subject matter, the inventors contemplate a method of predicting therapeutic outcome for immune therapy of a cancer that includes the steps of obtaining omics data from a tumor of a patient, identifying at least one of an APOBEC signature and a POLE signature in the omics data, quantifying expression of a plurality of genes associated with checkpoint inhibition from the omics data, and determining an MSI status from the omics data. In a further step, the APOBEC signature and/or POLE signature, the determined expression quantity of the plurality of genes, and the MSI status are then used to update or generate a patient profile that indicates a prediction of therapeutic outcome for the immune therapy of the cancer. Most typically, the immune therapy will include a checkpoint inhibition component and at least one of a vaccine component and a cell-based component.

Where desired, contemplated methods will further include a step of identifying at least one additional mutational signature. For example, suitable additional signatures include a kataegis signature, an Ig gene hypermutation signature, a smoking mutational signature, an age related mutational signature, a UV light mutational signature, and a DNA MMR related mutational signature.

Preferred omics data include whole genome sequencing data, RNA sequencing data, transcription level data, cfDNA sequence data, cfRNA sequence data, and proteomics data, and most typically at least two of these data that are preferably normalized against corresponding omics data from a healthy tissue of the same patient. APOBEC signatures typically include one or more of TpCpS→TpKpS, TpCpN→TpApN, and TpCpW→TpKpW, wherein S is C or G, K is G or T, N is C or G or A or T, and W is A or T, while preferred POLE signatures include TpCpT→TpApT and TpTpT→TpGpT.

With respect to the genes associated with checkpoint inhibition, it is generally contemplated that these genes include at least one, or at least two, or at least three, or at least four, or at least five of IDO, TDO, TIM3, CD40, LAG3, PD-L1, PD-L2, CTLA4, PD1, and IL2. While not limiting to the inventive subject matter, MSI status is preferably inferred from a quantity of neoepitopes that bind to an MHC complex of the patient.

In further contemplated aspects, the prediction of therapeutic outcome for the immune therapy of the cancer is a qualitative prediction. For example, presence of the APOBEC signature and/or the POLE signature is indicative of a favorable therapeutic outcome, a positive MSI is indicative of a favorable therapeutic outcome, and/or overexpression of the plurality of genes associated with checkpoint inhibition is indicative of a favorable therapeutic outcome. Where desired, contemplated methods may also include a step of determining the pathway activity for Th1 T cell activation, cytotoxic T cell activation, and/or natural killer cell activation.

Various objects, features, aspects and advantages of the inventive subject matter will become more apparent from the following detailed description of preferred embodiments.

BRIEF DESCRIPTION OF THE DRAWING

FIG. 1 exemplarily depicts a patient profile according to the inventive subject matter.

DETAILED DESCRIPTION

The inventors have now discovered that likely treatment outcome of cancer immune therapy can be predicted by computational analysis of patient omics data from tumor tissue where the immune therapy comprises administration of a cancer vaccine and/or cell based therapy in addition to checkpoint inhibitors. More particularly, the inventors discovered that the likely treatment outcome is associated with the overall immune status of the tumor, and especially with APOBEC and/or POLE mutational signatures, MSI status, and immune expression of genes associated with checkpoint inhibition.

While not limiting to the inventive subject matter, the inventors contemplate that the presence of APOBEC and/or POLE signatures were found to sharply increase the number of neoepitopes, possibly due to the specific mutational pattern in these signatures. Moreover, as APOBEC and/or POLE mutations also affect other genes associated with DNA repair, the frequency of mutations may abruptly increase once a critical number of APOBEC and/or POLE mutations is found. Thus, and viewed from a different perspective, APOBEC and/or POLE signatures may be particularly useful as a predictor of immunotherapy success as the number of SNVs will lead to a greater number of neoepitopes engendering stronger immune responses with vaccines targeting neoepitopes in an adaptive immune response, and NK cells and their derivatives targeting neoepitopes via ADCC in an innate immune response. As will be readily appreciated, such responses can be further complemented or enhanced with one or more checkpoint inhibitors.

In one exemplary aspect of the inventive subject matter, it is contemplated that prior to treatment of a cancer patient, a tumor biopsy is obtained from the patient and that an omics analysis is performed on the so obtained sample. Additionally, or alternatively, blood or other bodily fluid may be drawn from the patient, and cell free circulating RNA (cfRNA) and/or cell free circulating DNA (cfDNA) may be isolated from the blood or other biological fluid as is exemplarily described in WO 2016/077709.

In general, it is therefore contemplated that the omics analysis includes whole genome and/or exome sequencing, RNA sequencing and/or quantification, sequencing and/or quantification of cfRNA and/or cfDNA, and/or proteomics analysis. Among other options, it is noted that genomic analysis can be performed by any number of analytic methods, however, especially preferred analytic methods include WGS (whole genome sequencing) and exome sequencing of both tumor and matched normal sample, typically done using next generation sequencing. In the same way, cfDNA may be quantified and analyzed after isolation from the bodily fluid. Computational analysis of the sequence data may be performed in numerous manners. In most preferred methods, however, the analysis is performed in silico by location-guided synchronous alignment of tumor and matched normal samples from the same patient as, for example, disclosed in US 2012/0059670A1 and US 2012/0066001A1 using BAM files and BAM servers. Of course, alternative file formats (e.g., SAM, GAR, FASTA, etc.) are also expressly contemplated herein.

Likewise, RNA sequencing and/or quantification can be performed in all manners known in the art and may use various forms of RNA. For example, preferred materials include mRNA and primary transcripts (hnRNA), and RNA sequence information may be obtained from reverse transcribed poly $A^+$-RNA, which is in turn obtained from a tumor sample and a matched normal (healthy) sample of the same patient. Likewise, it should be noted that while poly $A^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis. Most typically, RNA quantification and sequencing is performed using qPCR and/or rtPCR based methods, although other methods (e.g., solid phase hybridization-based methods) are also deemed suitable. Viewed from another perspective, transcriptomic analysis may be suitable (alone or in combination with genomic analysis) to identify and quantify genes having a cancer and patient specific mutation. In the same way, cfRNA may be quantified and analyzed after isolation from the bodily fluid, and analysis typically includes a step of reverse transcription.

Similarly, proteomics analysis can be performed in numerous manners, and all known manners or proteomics analysis are contemplated herein. However, particularly preferred proteomics methods include antibody-based methods and mass spectroscopic methods (and especially selected reaction monitoring). Moreover, it should be noted that the proteomics analysis may not only provide qualitative or quantitative information about the protein per se, but may also include protein activity data where the protein has catalytic or other functional activity. Exemplary techniques for conducting proteomic assays include U.S. Pat. Nos. 7,473,532 and 9,091,651.

Of course, it should also be appreciated that the omics data may also be obtained from one or more computational resources, including publicly available or proprietary databases, and one or more sequencing devices. In such case, it should be appreciated that the omics data may be in numerous formats, including raw data (e.g., FASTA, FASTQ), processed data (e.g., BAM, SAM, GAR) or analyzed format that indicates changes (e.g., VCF). Likewise, where sequencing of nucleic acids is performed to obtain the omics data, such data may also be in various formats, including raw data formats, processed data formats, and formats from an analytic device. It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.).

The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

While there are numerous suitable mutational signatures it should be appreciated that particularly preferred mutational signatures have a frequency and base change patterns that produce a high rate of nonsense or missense mutations, which in turn lead to defective protein function and a higher rate of neoepitopes that are 'visible' to the immune system (i.e., that are bound by a patient's MHC complex for presentation on antigen presenting cells). Among other mutational signatures APOBEC and POLE signatures are especially preferred. Indeed, APOBEC mutations are frequently found in cancers (see e.g., Nat Genet 2013 September; 45(9): 970-976; Genome Res 2016; 26: 174-182). For example, APOBEC3A and 3B are cytidine deaminases of the APOBEC family, and are among the main factors causing mutations in human cancers. The APOBEC cytidine deaminase converts cytosine to uracil, which usually results in C→T or C→G mutations, and much less frequently, in C→A mutations. Moreover, fractions of the APOBEC-induced mutations occur as clusters in single-stranded DNA produced during repair of double-stranded breaks (DSBs), and such clusters ("kataegis") are contemplated suitable for use herein.

Therefore, as contemplated APOBEC signatures exhibit a transcriptional strand bias of mutations in exons and C>T and C>G exchange, especially suitable APOBEC signatures include TpCpS→TpKpS, TpCpN→TpApN, and TpCpW→TpKpW (S is C or G, K is G or T, N is C or G or A or T, and W is A or T). Moreover, it is noted that APOBEC mutagenesis is pervasive in cancers and correlates with APOBEC mRNA levels. Therefore, in addition to detection of APOBEC mutational signatures, expression levels (especially over-expression relative to corresponding normal tissue) of APOBEC genes is also particularly contemplated. Likewise, High expression of PD-1 ligands has been shown to be associated with kataegis mutational signatures and APOBEC3 alterations. Therefore, where APOBEC signatures are detected, it is especially contemplated that the omics analysis may further include sequence and transcriptional analysis of APOBEC genes and/or genes associated with checkpoint inhibition.

Indeed, APOBEC-dependent or APOBEC-like mechanisms may also be the etiologic agent for kataegis, give rise to MSI, and/or expression and presentation of neoepitopes that can be recognized and attacked by the immune system so long as no checkpoint inhibition is present as further discussed below. Viewed from a different perspective, mutations based on APOBEC may be a leading indicator of MSI and/or an increased number of immunologically visible neoepitopes, which may increase the likelihood of desirable treatment outcome where the treatment is performed using immune therapeutic agents.

Similarly, and in addition to the APOBEC mutational signatures, the inventors also contemplate POLE mutational signatures. Such signature typically exhibits a strand bias for C>A mutations at TpCpT context and T>G mutations at TpTpT context, and is commonly associated with some of most mutated cancer samples (samples exhibiting this mutational signature have also been termed ultra-hypermutators). As with the APOBEC signature, it is contemplated that these mutations have a frequency and base change patterns that produce a high rate of nonsense or missense mutations, which in turn lead to defective protein function and a higher rate of neoepitopes that are 'visible' to the immune system. Therefore, preferred POLE signature include TpCpT→TpApT and TpTpT→TpGpT. In still further contemplated aspects, mutational signatures also especially include POLD (see e.g., Nature Genetics 45, 136-144 (2013); published online EpubFeb (10.1038/ng.2503).

With respect to identification of APOBEC and POLE signatures, it should be noted that various manners are known to identify such signatures (see e.g., Nature 2013 Aug. 22; 500(7463): 415-421; Genome Res. 2016. 26: 174-182; Nat Genet. 2013 September; 45(9): 970-976; US 2012/0059670, or US 2012/0066001). However, it is particularly preferred that the tumor mutational signatures are identified against a matched normal control sample from the same patient using location guided synchronous alignment. Such alignment can provide output files (e.g., using vcf format) and information on type and location, as well as allow for classification into a particular mutational signature.

However, it should be appreciated that various other mutational signatures are also deemed suitable for use herein and suitable signatures include the smoking mutational signature (e.g., transcriptional strand bias for C>A mutations, CC>AA dinucleotide substitutions), the age related mutational signature (e.g., spontaneous deamination of 5-methylcytosine), the UV light mutational signature (e.g., CC>TT dinucleotide mutations at dipyrimidines), the DNA MMR related mutational signature (e.g., small indels), and Ig gene hypermutation signature. Further signatures, details, and considerations can be found at URL: cancer.sanger.ac.uk/cosmic/signatures and elsewhere (e.g., *BMC Med Genomics.* 2014; 7: 11.)

In addition, contemplated systems and methods may also include an overall estimate or determination of mutations in the genome (and/or exome and/or transcriptome), and it is generally contemplated that above a predefined threshold value, a mutation frequency may be indicative of increased likelihood of a desirable treatment outcome. For example, a mutation frequency of greater than 3 per MB (or greater than 2 per MB, or greater than 1 per MB, or greater than 0.5 per MB, or greater than 0.1 per MB) of coding DNA may be indicative of increased likelihood of a desirable treatment outcome. Such mutation frequency may be especially relevant where the mutation encodes a neoepitope that binds with an affinity of equal or less than 200 nM to the patient's MHC-I and/or MHC-II complex. For example, based on the identification of neoepitopes as being expressed and as binding to a patient's MHC-I and/or MHC-II complex with an affinity of equal or less than 200 nM, MSI may be inferred for cancers having a relatively high number of neoepitopes, typically at least 50, at least 80, at least 100, at least 150, at least 200, at least 250, at least 500, and even higher. Notably, when identifying cancer types by inferred MSI, the inventors observed that these cancers were shown to have a significantly higher likelihood to be responsive to treatment with a checkpoint inhibitor (e.g., UCEC, READ, BLCA, SKCM, LUSC, and COAD). Independent verification using different methodologies confirmed that these cancers were associated with MSI.

With respect to microsatellite instability (MSI) analysis the inventors contemplate that relatively large numbers of expressed neoepitopes can be used as a proxy indicator for MSI and certain genetic defects that are identifiable via their corresponding mutational signatures (e.g., APOBEC and conversion of cytidine to uracil) as further discussed in more detail below. As such, exome and/or high-throughput genome sequencing allows for rapid and specific identification of patient specific neoepitopes, particularly where the analysis also takes into account matched normal tissue of the same patient. For example, one method of determining MSI using quantification of expressed and MHC-bound neoepitopes is described in US 2017/0032082. However, other suitable methods of detecting and classifying MSI are also known in the art and described elsewhere (e.g., *Nature Communications* 2017; DOI: 10.1038/ncomms15180).

While determination of MSI and mutational patterns will provide valuable insights into availability of potential targets on a tumor, and particularly patient specific neoepitopes, such availability may be confounded by various immune system evading mechanisms by a tumor, and particularly by immune checkpoint inhibition and other cell-based mechanisms. To account for such inhibition, the inventors also contemplate that immune checkpoint expression is quantified for a tumor to gauge potential effects of immune therapeutic agents given to the patient. Immune checkpoint inhibition can be determined from omics data in various manners and all known manners are deemed suitable for use herein. Moreover, it should be appreciated that all receptors, ligands, and other mediators involved in checkpoint inhibition are deemed suitable for use herein and include those that activate or contribute to immune suppression and/or activation.

For example, especially contemplated receptors, ligands, and other mediators include IDO, TDO, TIM3, CD40, LAG3, PD-L1, PD-L2, CTLA4, PD1, and IL2. Moreover, it should be appreciated that molecules that indirectly activate or suppress immune response are also expressly contemplated herein. For example, it is known that STAT3 signaling has the potential to contribute to an immune suppressive environment by several mechanisms, including suppression of dendritic cell (DC) maturation and function, enhanced myeloid derived suppressor cell (MDSC) activity, and suppression of T-cell mediated antitumor activity. Thus, measurement of regulatory components may further provide insight into outcome prediction.

It should be appreciated that the immune checkpoint components may be quantified using various manners, and that all manners known in the art are deemed suitable for use herein. For example, immune checkpoint components may be quantified using omics data, and especially transcriptomics data. However, in at least some aspects of the inventive subject matter, omics data for genes associated with checkpoint inhibition are obtained from a blood sample using cfRNA and/or cfDNA. Alternatively, or additionally, immune checkpoint components may be quantified using SRM mass spectroscopy, or immunohistochemical methods, either directly from the tumor, from processed tumor tissue, or from blood.

Where desired, the omics data may also be processed to obtain pathway activity and other pathway relevant information using various systems and methods known in the art. However, particularly preferred systems and methods include those in which the pathway data are processed using probabilistic graphical models as described in WO/2011/139345 and WO/2013/062505, incorporated by reference herein. Thus, it should be appreciated that pathway analysis for a patient may be performed form a single patient sample and matched control, which will significantly improve and refine analytic data as compared to single omics analysis that is compared against an external reference standard. In addition, the same analytic methods may further be refined with patient specific history data (e.g., prior omics data, current or past pharmaceutical treatment, etc.).

In particularly preferred aspects of the inventive subject matter, differentially activated pathways and pathway elements in the output of the pathway analysis are then ranked, and the most significant portion (e.g., top 500 features, top 200 features, top 100 features) is analyzed for feature sets associated with immunogenicity of a tumor. For example, an especially contemplated feature set that corresponds to presence or activity of tumor infiltrating lymphocytes (especially cytotoxic T cells, natural killer cells) and Th1-type T cells and associated Th1 signaling may be used to evaluate positive correlation with high tumor immunogenicity while another feature set that corresponds to Th2-type T cells and associated Th2 signaling may be used to evaluate negative correlation with tumor immunogenicity. Additionally, further feature sets include genes and activities related to inflammation, innate immunity, etc.

Prediction of likely treatment outcome will then be a qualitative and/or quantitative composite score that takes into account one or more mutational signatures (and especially APOBEC and/or POLE signatures, the MSI status, and immune checkpoint expression data. In most typical aspects of the inventive subject matter, an MSI status that is indicative of microsatellite instability will weigh in favor of a positive treatment outcome. Likewise, detection of one or more mutational signatures (with high frequency of SNPs, and especially SNPs that change the protein sequence, that are expressed at relatively high level, and that are presented via the patient's MHC) will weigh in favor of a positive treatment outcome. In addition, it is noted that determination of overexpression of one or more components for checkpoint inhibition will also weigh in favor of a positive treatment outcome. FIG. 1 depicts an exemplary updated patient record that reflects contemplated systems and methods as presented herein.

In the example of FIG. 1, microsatellites were deemed instable by quantification of expressed and MHC-bound neoepitopes as described in US 2017/0032082 using a threshold value of 100 HLA matched neoepitopes, and positive treatment outcome ('immunotherapy permissible': yes) was predicted for microsatellite instability, while negative treatment outcome ('immunotherapy permissible': no) was predicted for stable microsatellites. However, it should be appreciated that microsatellite instability can also be determined using other known protocols (e.g., *Nature Communications* 2017; DOI: 10.1038/ncomms15180).

APOBEC and POLE mutation signatures were identified by analysis of the bases directly adjacent to a mutated base position, and exposure to APOBEC and POLE mutation signatures was calculated using non-negative matrix factorization (NMF) on the counts of mutated triplets identified in the tumor sample, and substantially followed a protocol as described elsewhere (*Nature* 2013 Aug. 22; 500(7463): 415-421). However, it should be appreciate that various alternative methods of identification of APOBEC and/or POLE signatures are also deemed suitable and include those described in *Genome Res.* 2016. 26: 174-182; *Nat Genet.* 2013 September; 45(9): 970-976; US 2012/0059670, and US 2012/0066001. Regardless of the manner of detection, presence of an APOBEC signature predicted positive treatment outcome ('immunotherapy permissible': yes). Likewise, presence of an POLE signature predicted positive treatment outcome ('immunotherapy permissible': yes). Absence of the mutational signatures predicted negative treatment outcome ('immunotherapy permissible': no).

In the example of FIG. 1, an overall genomic mutation rate of above 1.0 per Megabases of coding DNA were deemed immunotherapy permissive, while genomic mutation rates below 1.0 per Megabases of coding DNA were deemed not immunotherapy permissive. However, it should be noted that other cut-off values are also deemed suitable, and especially contemplated overall genomic mutation rates that separate immunotherapy treatment permissive from non-permissive are 0.5, 1.5, 2.0, 3.0, 5.0, and hypermutation rates above 5.0.

Immune checkpoint expression was deemed immunotherapy permissive where at least 30% of all tested genes with function in checkpoint inhibition were expressed or even overexpressed (e.g., more than 20% as measured by TPM relative to matched normal from the same patient). While TIM-3, LAG-3, PD-1, PD-L1, PD-L2, IDO, TDO, CTLA4, IL2, and CD40 are particularly preferred, numerous other genes related to checkpoint inhibition are also contemplated suitable for use herein. Likewise, immune checkpoint expression may also be deemed immunotherapy permissive where at least 40%, or 50%, or 60%, or 70%, or 80% of all tested genes with function in checkpoint inhibition are expressed or overexpressed.

Treatment outcome will typically be with respect to immunotherapy, and particularly with respect treatments that include a vaccine component, a cell-based component, and/or a drug that interferes with checkpoint inhibition and/or immunostimulatory drugs. For example, suitable cell-based treatment includes treatments with recombinant or transfected NK cells, dendritic cells, or T cells expressing neoepitopes or chimeric antigen receptors binding to one or more neoepitopes). Thus, especially contemplated cell based treatments include administration of NK92 cells and derivatives thereof (e.g., aNK cells, haNK cells and tank cells, commercially available from NantKwest, 9920 Jefferson Blvd. Culver City, CA 90232). On the other hand, particularly preferred vaccine based treatments include recombinant viral, bacterial, or yeast those that comprise a nucleic acid that encodes one or more neoantigens, preferably together with immunostimulatory molecules and/or checkpoint inhibitors. Among other options, suitable recombinant viral vaccines include adenovirus-based vaccines (and especially Ad5-based viruses with reduced immunogenicity as described in US 2017/0165341 or US 2017/0065693), while preferred bacterial vaccines include those produced in *E. coli* having a reduced endotoxin (e.g., commercially available from Lucigen, 2905 Parmenter St., Middleton, WI 53562), and preferred yeast vaccines are based on *S. cerevisiae*.

Without wishing to be bound by any particular theory or hypothesis, the inventors contemplate that the presence of an APOBEC and/or POLE signature in addition to other mutational patterns such as MSI and overall mutation rate substantially increased accuracy of treatment outcome prediction where a cancer patient is treated with immunotherapy (that typically includes a vaccine component (e.g., neoepitope based adenoviral, yeast, or bacterial vaccine), a cell-based component (e.g., NK cell, aNK cell, or haNK cell based), and/or administration of one or more checkpoint inhibitors. Most notably, APOBEC and/or POLE signatures frequently resulted in a substantial upshift in missense neoepitopes with concurrent reduction of DNA repair, which generated a substantially increased number of targets that are 'visible' to the immune system (i.e., can be presented on antigen presenting cells). Such scenario is particularly beneficial for immunotherapy where multiple checkpoint inhibition related genes are also present or overexpressed, which renders the tumors more susceptible to treatment with checkpoint inhibitors. Viewed from a different perspective, consideration of APOBEC and/or POLE signatures in the context of other mutational events substantially increases accuracy of predicted treatment outcome of a cancer with immunotherapy.

Further aspects, methods, and contemplations are disclosed in co-pending US provisional application with the Ser. No. 62/240,494, filed 12 Oct. 2015, and which is incorporated by reference herein.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a cancer patient with immune therapy, comprising:
obtaining, from the cancer patient, a tumor sample and a matched normal sample;

obtaining omics data from the tumor sample and matched normal sample, wherein the omics data comprises whole genome and/or exome sequencing data, RNA sequencing data, and transcriptomics data;

comparing, in silico, the whole genome and/or exome sequence of the tumor sample with the matched normal sample to identify at least one of an APOBEC mutational signature and a POLE mutational signature, wherein the APOBEC signature is selected from the group consisting of: TpCpS→TpKpS, TpCpN→TpApN, and TpCpW→TpKpW, wherein S is C or G, K is G or T, N is C or G or A or T, and W is A or T, and/or wherein the POLE signature is selected from the group consisting of: TpCpT→TpApT and TpTpT→TpGpT;

comparing, in silico, the whole genome transcriptomics data of the tumor sample with the matched normal sample to quantify over-expression of a plurality of genes associated with checkpoint inhibition, wherein the genes associated with checkpoint inhibition are selected from the group consisting of: IDO, TDO, TIM3, CD40, LAG3, PD-L1, PD-L2, CTLA4, PD1, and IL2;

determine a positive microsatellite instability (MSI) status from the sequenced whole genome and/or exome; and treating the cancer patient with immune therapy upon identifying APOBEC or POLE mutational signature, overexpression of the plurality of genes associated with checkpoint inhibition, and/or a positive MSI, wherein the immune therapy includes a checkpoint inhibitor.

2. The method of claim 1 further comprising a step of identifying at least one additional mutational signature.

3. The method of claim 2 wherein the additional mutational signature is a kataegis signature, an Ig gene hypermutation signature, a smoking mutational signature, an age related mutational signature, a UV light mutational signature, or a DNA MMR related mutational signature.

4. The method of claim 1 wherein the whole genome and/or exome omics data are normalized against whole genome and/or exome omics data from a healthy tissue of the same patient.

5. The method of claim 1 wherein the plurality of genes are at least five genes.

6. The method of claim 1 wherein the MSI status is inferred from a quantity of neoepitopes that bind to an MHC complex of the patient.

7. The method of claim 1 further comprising a step of determining pathway activity for Th1 T cell activation, cytotoxic T cell activation, and natural killer cell activation.

* * * * *